United States Patent [19]

Shinagawa et al.

[11] Patent Number: 4,948,534

[45] Date of Patent: Aug. 14, 1990

[54] DERIVATIVES OF β-AMINO-γ-TRIMETHYLAMMONIO-BUTYRATE AND THEIR PRODUCTION AND USE

[75] Inventors: Susumu Shinagawa; Tsuneo Kanamaru, both of Osaka; Setsuo Harada, Kawanishi; Mitsuko Asai, Osaka, all of Japan

[73] Assignee: Takeda Chemical Industries, Ltd., Osaka, Japan

[21] Appl. No.: 423,555

[22] Filed: Oct. 16, 1989

Related U.S. Application Data

[63] Continuation of Ser. No. 830,986, Feb. 19, 1986, abandoned, which is a continuation of Ser. No. 613,416, May 24, 1984, abandoned, which is a continuation-in-part of Ser. No. 442,368, Nov. 17, 1982, Pat. No. 4,521,432.

[30] Foreign Application Priority Data

Nov. 26, 1981 [WO] PCT Int'l Appl. ... PCT/JP81/00355
Jul. 28, 1982 [WO] PCT Int'l Appl. ... PCT/JP82/00291
Oct. 15, 1982 [WO] PCT Int'l Appl. ... PCT/JP82/00409
May 25, 1983 [JP] Japan ................................... 58-93179
May 15, 1984 [JP] Japan ................................... 59-96773

[51] Int. Cl.$^5$ .............................................. C09F 5/06
[52] U.S. Cl. ................................... 260/399; 260/401; 260/404.5
[58] Field of Search ....................... 260/404.5, 399, 401

[56] References Cited

U.S. PATENT DOCUMENTS 4,521,432  6/1985  Kanamaru et al. .................. 514/556

*Primary Examiner*—Richard L. Raymond
*Assistant Examiner*—Raymond Covington
*Attorney, Agent, or Firm*—Wegner & Bretschneider

[57] ABSTRACT

A compound of the formula:

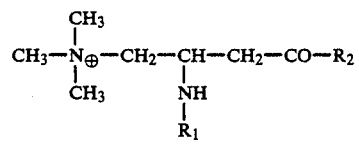

wherein $R_1$ is hydrogen, alkyl or acyl, $R_2$ is hydroxy, alkoxy or amino, is useful as an antidiabetic agent.

21 Claims, 2 Drawing Sheets

DERIVATIVES OF β-AMINO-γ-TRIMETHYLAMMONIO-BUTYRATE AND THEIR PRODUCTION AND USE

This application is a continuation of United States application Ser. No. 830,986 filed Feb. 19, 1986, which is a continuation of Ser. No. 613,416 Filed May 24, 1984, now abandoned, which is a C-I-P of application Serial No. 442,368 filed Nov. 17, 1982 now U.S. Pat. No. 4,521,432.

This invention relates to derivatives of β-amino-γ-trimethylammonio-butyrate and their production and use.

There has for sometime been a demand for a more effective antidiabetic drug having a new mode of action for the treatment of diabetes and its complications, the incidence of which has been on the steady increase. Thus, in diabetes, as an insulin deficiency promotes a liberation of fatty acids in the adipose tissue, there occurs an increased supply of fatty acids to the liver and as the decomposition of fatty acids is concurrently promoted, the production of ketone compounds is stimulated, leading to the so-called ketonemia. In the extrahepatic tissues, the utilization of glucose is poor and the ketone compounds so produced are used as energy sources. Therefore, it is expected that if the decomposition of fatty acids is inhibited, the production of ketone compounds will be attenuated and, consequently, the utilization of glucose be promoted so that blood sugar levels are ultimately decreased. In other words, a specific inhibitor of fatty acid degradation would be of value as a new antidiabetic drug relying on a new mechanism of action.

In view of these background facts, the present inventors made an extensive study for the development of a new antidiabetic and discovered that derivatives of the compound of the formula:

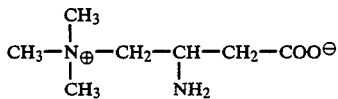

are substances capable of inhibiting the decomposition of fatty acids, and have completed the present invention.

The present invention is directed to:
(1) a compound of the formula:

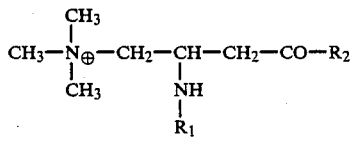

wherein $R_1$ is a hydrogen atom or a substituted or unsubstituted hydrocarbon containing residue and $R_2$ is a group represented by the formula $-OR_3$ (in which $R_3$ is a hydrogen atom or a substituted or unsubstituted hydrocarbon residue) or by the formula $-NH-R_4$ (in which $R_4$ is a hydrogen atom or a substituted or unsubstituted hydrocarbon residue), provided that when $R_1$ is a hydrogen atom or an acetyl group, $R_2$ is not a hydroxy group; or a pharmaceutically acceptable salt thereof;

(2) a method of producing the compound (I) or a salt thereof, which comprises subjecting a compound of the formula:

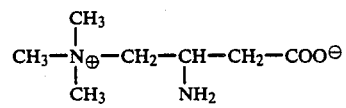

or a salt thereof to hydrocarbon residue introduction reaction, esterification reaction and/or amidation reaction;

(3) an antidiabetic agent which contains an antidiabetically effective amount of the compound (I) or a pharmaceutically acceptable salt thereof and a pharmaceutically acceptable carrier, excipient or diluent therefor, (4) a compound in the optically active D-form which is represented by the formula:

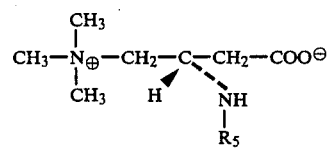

wherein $R_5$ is a hydrogen atom or an acetyl group; or a salt thereof; and (5) a method of producing a compound of the formula

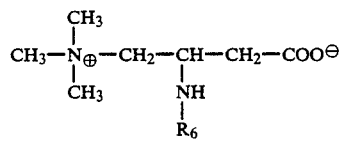

wherein $R_6$ is $-COCH_2CH_3$ or $-COCH_2CH_2CH_3$, which comprises cultivating a microorganism belonging to the genus Emericella and capable of producing the compound (IV) in a culture medium so as to cause formation and accumulation of the compound (IV) in the culture medium and isolating said compound.

In the present specification, the compound of the formula (I) in which $R_1$ is acetyl and $R_2$ is hydroxy, when in the optically active L-form, is sometimes referred to as "FA-5859". The compound of the formula (I) in which $R_1$ is hydrogen and $R_2$ is hydroxy is β-amino-γ-trimethylammonio-butyrate, and when in the optically active L-form it is sometimes referred to as "deacetyl FA-5859".

In the above formulas, the hydrocarbon containing residue which is represented by any of $R_1$, $R_3$ and $R_4$ and may optionally be substituted may be any of carbon-containing groups and the carbon atom of which is available for bonding.

More specifically, said containing hydrocarbon residue includes, among others, alkyl, alkenyl, aryl, aralkyl and heterocyclic groups.

Said alkyl group preferably contains 1 to 20 carbon atoms. Examples are methyl, ethyl, n-propyl, isopropyl, cyclopropyl, n-butyl, isobutyl, tert-butyl, cyclobutyl, pentyl, isopentyl, cyclopentyl, hexyl, isohexyl, cyclohexyl, heptyl, cycloheptyl, octyl, cyclooctyl, nonyl, decyl, undecyl, dodecyl, tridecyl, tetradecyl, pentadecyl, hexadecyl, heptadecyl, octadecyl, nonadecyl and eicosyl.

The above-mentioned alkenyl preferably contains 1 to 18 carbon atoms and is, for example, vinyl, propenyl, allyl, butenyl or oleyl.

The above-mentioned aryl is, for example, phenyl or naphthyl.

The above-mentioned aralkyl is, for example, benzyl, α-methylbenzyl, phenethyl, diphenylmethyl, 1-phenylpropyl or 1-phenylbutyl.

The above-mentioned heterocyclic group is, for example, pyridyl, pyrazinyl, pyrrolidinyl or piperidyl.

The alkyl group mentioned above as a hydrocarbon residue may be substituted, for instance, by lower alkoxy, oxo, halogen, hydroxy, nitro, amino, cyano, sulfo, aryl and/or aralkyloxy.

The alkenyl group mentioned above as a hydrocarbon residue may be substituted, for instance, by lower alkoxy, oxo, halogen, hydroxy, aryl.

The aryl, aralkyl and heterocyclic groups each mentioned above as a hydrocarbon residue may be substituted, for example, by lower alkyl, lower alkoxy, oxo, halogen, hydroxy, nitro, amino, cyano, sulfo and/or phenyl.

The lower alkyl mentioned above as a substituent preferably contains 1 to 6 carbon atoms and includes, among others, methyl, ethyl, n-propyl, isopropyl, n-butyl, isobutyl, tert-butyl, n-pentyl, isopentyl, cyclopentyl, hexyl, isohexyl and cyclohexyl.

The lower alkoxy mentioned above as a substituent preferably contains 1 to 6 carbon atoms. Examples are methoxy, ethoxy, propoxy, isopropoxy, n-butoxy, secbutoxy, tert-butoxy, n-pentyloxy, isopentyloxy and n-hexyloxy, and more preferably those containing 1 to 4 carbon atoms.

The above-mentioned halogen as a substituent is, for example, chlorine, bromine, iodine or fluorine.

The aryl mentioned above as a substituent is, for example, phenyl.

The aralkyloxy mentioned above as a substituent is, for example, phenyl-$C_{1-4}$ alkyloxy. The $C_{1-4}$ alkyl in the above-mentioned phenyl-$C_{1-4}$ alkyloxy is, for example, methyl, ethyl, n-propyl, isopropyl, n-butyl, isobutyl or tert-butyl. As the aralkyloxy, benzyloxy is more preferable.

Preferable examples of the hydrocarbon residue in the substituted or unsubstituted hydrocarbon residue of $R_1$ are alkyl of 1 to 6 carbon atoms and acyl of the formula —CO—$R_7$ (wherein $R_7$ is hydrogen or alkyl of 1 to 17 carbon atoms).

Examples of the above-mentioned alkyl of 1 to 6 carbon atoms are methyl, ethyl, n-propyl, isopropyl, n-butyl, isobutyl, t-butyl, n-pentyl, isopentyl, n-hexyl and isohexyl.

Examples of the above-mentioned $C_{1-17}$ alkyl in the symbol $R_7$ are methyl, ethyl, n-propyl, isopropyl, cyclopropyl, n-butyl, isobutyl, tert-butyl, cyclobutyl, pentyl, isopentyl, cyclopentyl, hexyl, isohexyl, cyclohexyl, heptyl, cycloheptyl, octyl, cyclooctyl, nonyl, decyl, undecyl, dodecyl, tridecyl, tetradecyl, pentadecyl, hexadecyl and heptadecyl.

The above-mentioned alkyl of 1 to 6 carbon atoms and acyl group of the formula —CO—$R_7$ may be substituted by lower alkoxy, halogen, hydroxy, nitro, amino, cyano, sulfo, aryl or aralkyloxy.

As examples of said lower alkoxy, halogen, aryl and aralkyloxy, there are mentioned those described above.

As preferable examples of the group of the formula —CO—$R_7$ substituted by lower alkoxy, amino, aryl or aralkyloxy, when substituted by lower alkoxy there is mentioned methoxycarbonyl, ethoxycarbonyl, propoxycarbonyl, isopropoxycarbonyl, n-butoxycarbonyl, secbutoxycarbonyl and tert-butoxycarbonyl, when substituted by amino there is mentioned carbamoyl, when substituted by aryl there is mentioned benzoyl, when substituted by aralkyloxy there is mentioned benzyloxycarbonyl, respectively.

Preferred examples of $R_2$ in the above formula are hydroxy, $C_{1-6}$ lower alkoxy or —$NH_2$.

Examples of the above-mentioned $C_{1-6}$ lower alkoxy are methoxy, ethoxy, propoxy, isopropoxy, n-butoxy, secbutoxy, tert-butoxy, n-pentyloxy, isopentyloxy and n-hexyloxy.

The number of said substituents is preferably one to three.

The hydrocarbon residue introduction reaction according to the invention is effected by using a halide carrying the desired hydrocarbon residue or an alkyl sulfate such as dimethyl sulfate. The halogen in said halide is, for example, bromine, iodine or chlorine. The reaction is generally carried out in a solvent such as tetrahydrofuran, dioxane, water, dimethyl formamide, chloroform, acetonitrile, ethyl acetate or pyridine, or in a mixture of such solvents. The alkylation reaction, for instance, is generally carried out in the presence of a base, such as an alkali metal hydroxide or sodium hydride, at a temperature generally in the range of about $-10°$ to $80°$ C. (but not particularly limited thereto) for about 5 to 48 hours, preferably about 5 to 12 hours.

In cases where the above-mentioned hydrocarbon residue $R_1$ is an oxo-substituted alkyl, the above hydrocarbon residue introduction reaction may be carried out in the conventional manner of acylation.

As the acylating agent to be used in said acylation reaction, there is used an acylating agent containing an oxo-substituted alkyl group (acyl group) as represented by $R_1$. Said acylating agent includes conventional acylating agents, such as halides, anhydrides, active esters and azides each derived from an acid containing said acyl group. The halogen of said halides is, for example, chlorine or bromine. Said active esters include, among others, p-nitrophenyl esters and N-hydroxysuccinimide esters. Said acylation reaction is preferably carried out in a solvent. Said solvent includes, among others, water, acetone, tetrahydrofuran, dioxane, acetonitrile, diethyl ether, chloroform, dichloromethane, ethyl acetate, dimethylformamide and pyridine. Such solvents may be used either alone or in the form of a mixture. The acylating agent is used generally in an amount of about 1 to 5 moles, preferably about 1 to 1.5 moles, per mole of the starting compound. Generally, the acylation is advantageously carried out in the presence of a base such as an alkali metal hydrogen carbonate, an alkali metal carbonate, an alkali metal hydroxide, a trialkylamine or pyridine. The reaction temperature is not critical. Generally, however, the reaction is carried out about $-10°$ to $+50°$ C., preferably at about $5°$ to $30°$ C., for about 1 to 48 hours, preferably about 1 to 12 hours. The pH in the reaction system is kept at about 7 to 11, preferably about 8 to 9.

The esterification reaction in the practice of the invention can be carried out in the conventional manner. Thus, for instance, in accordance with one mode of carrying out said esterification reaction, the starting compound is suspended in an alcohol which contains an alkoxy group represented by $R_2$ and, then, a gas such as hydrogen chloride gas is blown into the suspension. In this mode, the alcohol is used in large excess of the starting compound. The reaction temperature is generally about 0° to 80° C., preferably about 25° to 60° C., and the reaction time, namely gas introduction period, is about 1 to 12 hours, preferably about 1 to 4 hours. The esterification reaction may also be effected by suspending the starting compound in an alcohol (which contains an alkoxy group represented by $R_2$) with an inorganic or organic acid, such as hydrogen chloride, sulfuric acid or toluenesulfonic acid, added thereto in advance, and treating the resulting mixture at about 0° to 100° C., preferably about 25° to 80° C., or with heating under reflux, for about 5 to 48 hours, preferably 5 to 12 hours.

In accordance with another mode of said esterification, an alcohol containing an alkoxy group represented by $R_2$ is reacted with thionyl chloride, acetyl chloride, sulfinyl chloride, trifluoroacetic acid anhydride or the like at a low temperature of about $-40°$ to $-5°$ C., preferably about $-20°$ to $-5°$ C., and then the starting compound is added to the above reaction mixture for treatment. The treatment (reaction) is carried out at about 0° to 100° C., preferably about 25° to 80° C., or with heating under reflux, for about 1 to 48 hours, preferably about 4 to 12 hours.

The amidation according to the invention is effected, for example, by bringing the above ester into contact with ammonia or an amine of the formula $NH_2$—$R_4$ wherein $R_4$ is as defined above. For said reaction, ammonia or the amine is used in an amount of about 1 to 20 moles, preferably about 2 to 10 moles, per mole of the ester. The reaction is carried out at about 0° to 100° C., preferably about 25° to 60° C., for 12 to 72 hours, preferably 24 to 48 hours.

The amidation may also be effected, for example, by activating the carboxyl group of the starting compound and then bringing the activation product into contact with ammonia or the above-mentioned amine. Said activation is effected by treating the starting compound, for example, with phosphorus pentachloride, thionyl chloride or the like for conversion of said compound to the acid chloride form, or with isobutyloxycarbonyl chloride, ethoxycarbonyl chloride or the like for conversion of said compound to the mixed acid anhydride form, or by converting said compound to an active ester with p-nitrophenol, N-hydroxysuccinimide, N-hydroxy-5-norbornene-2,3-dicarboximide or the like. The thus-activated starting compound is reacted with about 1 to 2 moles, per mole of the activated starting compound, of ammonia or the amine. The reaction is carried out at about 0° to 100° C., preferably about 25° to 60° C., for about 12 to 24 hours.

In accordance with a further mode, the amidation may be carried out by contacting the starting compound with ammonia or the amine in the presence of a condensing agent such as a carbodiimide (e.g. dicyclohexylcarbodiimide), carbonylimidazole or N-ethyl-5-isoxazolium-3-sulfonic acid salt. The condensing agent is used in an amount of 1 to 3 moles, preferably 1.2 to 1.5 moles, per mole of the starting compound. The reaction is carried out at about $-10°$ to $+50°$ C., preferably about $-5°$ to $+25°$ C., for about 5 to 48 hours, preferably about 10 to 24 hours.

The thus-produced compound (I) is separated and/or collected from the reaction mixture by the conventional method, such as extraction with an organic solvent (e.g. chloroform, n-butanol) or column chromatography using an ion exchange resin or an adsorbent resin, among others.

Those compounds (I) in, which $R_1$ is a substituted or unsubstituted hydrocarbon containing residue and $R_2$ a group of the formula —$OR_3$ wherein $R_3$ is a hydrocarbon residue which may optionally be substituted or the formula —NH—$R_4$ wherein $R_4$ is a hydrogen atom or a hydrocarbon residue which may optionally be substituted can be produced by (i) subjecting the compound (II) or a salt thereof to hydrocarbon residue introduction reaction and then subjecting the resulting compound to esterification or amidation or (ii) subjecting the compound (II) or a salt thereof esterification cation or amidation and then subjecting the resulting compound to hydrocarbon residue introduction reaction.

The compound (III) in the optically active D form can be produced for example by the following procedure:

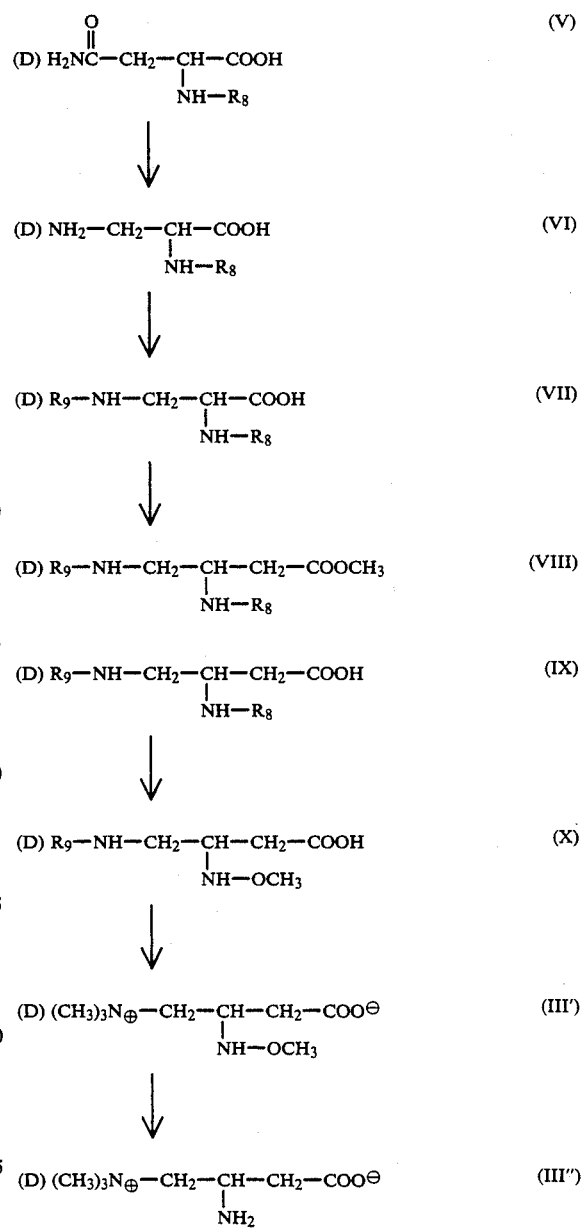

In the above formulas, the group $R_8$ means a protective group other than acetyl. The protective group $R_8$ is exemplified by t-butyloxycarbonyl, benzyloxycarbonyl, p-methoxybenzyloxycarbonyl, p-nitrobenzyloxycarbonyl.

$R_9$ is a protective group which is eliminable under conditions different from those for eliminating the protective group $R_8$. Examples of such protective group $R_9$ are benzyloxycarbonyl, tert-butoxycarbonyl, p-nitrobenzyloxycarbonyl, p-methoxybenzyloxycarbonyl, trityl, tosyl, tert-amyloxycarbonyl, isobornyloxycarbonyl, diphenylphosphinyl, α-nitrophenylsulfenyl and phthaloyl.

The compound (V) is a protected D-asparagine in which the α-amine group is protected by a protective group represented by $R_8$. The compound (V) can be produced by reacting D-asparagine with a protective group introducing reagent containing $R_8$ ($R_8$—X wherein R is, for instance, halogen, active ester or amide). The reaction is carried out in water or a mixture of water and an organic solvent such as tetrahydrofuran, acetonitrile or dioxane, in the presence of a base such as an alkali metal hydroxide (e.g. NaOH, KOH) or triethylamine, at about 0° C. to 25° C. for about 1 to 24 hours.

For the production of compound (VI) from compound (V), the compound (V) is reacted with bistrifluoroacetoxyphenyliodine in a mixed solvent composed of water and dimethylformamide. The reaction is carried out in the presence of a base, such as triethylamine or an alkali metal hydroxide, at about 0° to 50° C., preferably about 10° to 5° C., for about 10 to 48 hours.

For the production of compound (VII) from compound (VI), the compound (VI) is acylated at the amino group thereof with an agent for introducing a protective group represented by $R_9$. Thus, said protective group ($R_9$) introducing agent and the compound (VI) are reacted in water, tetrahydrofuran, acetonitrile or dimethylformamide or a mixed solvent composed of these, at about 0° to 50° C. for about 5 to 24 hours. The reaction is generally carried out in the presence of a base such as triethylamine or sodium hydrogen carbonate.

For the production of compound (VIII) from compound (VII), the carboxylic acid is first converted to a mixed acid anhydride, which is then diazonized and then subjected to Wolff rearrangement.

The mixed acid anhydride is produced by reacting the compound (VII) with an acid chloride such as ethyl chlorocarbonate, methyl chlorocarbonate, propyl chlorocarbonate, butyl chlorocarbonate or isobutyl chlorocarbonate, in an organic solvent such as ethyl acetate, methyl acetate, dioxane, tetrahydrofuran or acetonitrile. The reaction may be carried out in the presence of an organic base such as N-methylmorpholine, N-ethylmorpholine, triethylamine, trimethylamine or pyridine. The reaction temperature is about −20° C. to 30° C., preferably about −10° C. to 0° C.

The diazonation is carried out by reacting the mixed acid anhydride with diazomethane in an organic solvent such as ethyl acetate, methyl acetate, tetrahydrofuran, dioxane, acetonitriel or diethyl ether, at a temperature of about −20° C. to 30° C., preferably about −10° C. to 25° C., for about an hour to 24 hours. Diazomethane may either be blown into the solution or be added to the solution as a saturated solution of diazomethane in an organic solvent such as diethyl ether or ethyl acetate.

The Wolff rearrangement is carried out by reacting the diazonized compound with a silver salt of benzoic acid or acetic acid, for instance, dissolved in an organic base such as trimethylamine, triethylamine, N-methylmorpholine, N-ethylmorpholine or pyridine, at about −5° C. to 50° C., preferably about 0° C. to 27° C., in the dark, for about 30 minutes to 10 hours.

The compound (IX) is produced by saponifying the compound (VIII). Said saponification is carried out by contacting the compound (VIII) with a hydroxide of sodium, potassium or barium, for instance, in water, an organic solvent such as methanol, ethanol, dioxane, tetrahydrofuran or acetonitrile, or a mixed solvent composed of water and an organic solvent such as mentioned above, at about −10° C. to 50° C., preferably about 0° C. to 27° C., for about an hour to 5 hours.

The compound (X) is produced from the compound (IX) by selective elimination of $R_8$ and introduction of acetyl group.

Said elimination can be performed by a method conventionally used in the peptide syntheses such as hydrolysis, catalytic reduction, or acid treatment. The hydrolysis can be effected by any method that is conducive to a cleavage of an amide bond. For example, methods employing an acid, a base or an ion exchange resin may be mentioned. Examples of said acid include inorganic acids such as sulfuric acid and hydrochloric acid and examples of said base include potassium hydroxide, sodium hydroxide and barium hydroxide. Examples of said ion exchange resin include Dowex-50 (Dow Chemical, U.S.A.), Amberlite IR-120 (Rohm and Haas Co., U.S.A.) and Diaion-SK1A and SK1B (Mitsubishi Chemical Industries Ltd., Japan).

When the acid is employed, the reaction is preferably conducted in aqueous solution and when an aqueous solvent is employed, it is preferably a mixture of water with methanol, ethanol, butanol or the like. The reaction is conducted generally at about 60° to 200° C. and preferably at about 90° to 120° C., generally for about 30 minutes to 30 hours and preferably for about 3 to 16 hours.

When the base is employed, the reaction is desirably conducted in aqueous solution. This reaction is also desirably conducted in an aqueous solvent such as a mixture of water with methanol, ethanol, butanol or the like. This reaction is carried out generally at about 60° to 200° C. and preferably at about 90 to 120° C., generally for about 30 minutes to 30 hours and preferably for about 3 to 16 hours.

When the ion exchange resin is employed, the resin is suspended in an aqueous solution of the starting material compound and the suspension is heated. This reaction is conducted generally at 60° to 200° C. and preferably at about 90° to 120° C., generally for about 30 minutes to 30 hours and preferably for about 3 to 16 hours.

Said catalytic reduction is carried out in an alcohol such as methanol or ethanol or a mixed solvent composed of water and an alcohol, in the presence of a catalyst such as palladium black or palladium-on-carbon introducing hydrogen gas into the reaction system, if necessary under pressure. The reaction is carried out at 0° C. to 50° C., preferably at 20° to 30° C., and the reaction time is within about 0.5 to 5 hours, preferably within about 1 to 3 hours.

The acid to be used in said acid treatment is, for example, hydrogen bromide-acetic acid, hydrochloric acid, acetic acid, hydrochloric acid-dioxane, trifluoroacetic acid, methanesulfonic acid or trifluoromethanesulfonic acid. The temperature of the acid treatment should advisably be selected depending upon the acid used within the range of about −10° C. and 50° C., preferably about 0° C. to 25° C., and the reaction time within the range of about 30 minutes to 24 hours.

The acetylation is effected by reacting the starting compound with acetic anhydride, or a mixed acid anhydride prepared by reacting acetyl chloride or acetic acid with an alkoxycarbonyl chloride such as methyl chlorocarbonate, ethyl chlorocarbonate, butyl chlorocarbonate, propyl chlorocarbonate or isobutyl chlorocarbonate, in water or a mixed solvent composed of water and an organic solvent such as acetone, dioxane, acetonitrile, dimethylformamide or tetrahydrofuran. The reaction may be conducted in the presence of a deacidifying agent such as an organic base (e.g. pyridine, triethylamine, trimethylamine) or a hydroxide, oxide or bicarbonate of an alkali or alkaline earth metal (e.g. sodium, potassium, calcium). The reaction temperature is about −10° C. to 50° C., preferably about 0° C. to 25° C.

The trimethylation of compounds (III') from the compound (X) in accordance with the present invention is carried out, for example, by reacting compound (X) with dimethyl sulfate, methyl bromide, methyl chloride or methyl iodide in water or a mixture of water and an organic solvent such as acetonitrile, dioxane, tetrahydrofuran or dimethylformamide. The reaction may be performed in the presence of, for instance, a hydroxide or oxide of an alkali or alkaline earth metal such as sodium, potassium or calcium, as necessary. The reaction temperature is about −10° C. to 50° C., preferably about 0° C. to 20° C.

The desired products yielded by either of the above reactions can be isolated and purified by conventional separation and/or purification techniques, such as chromatography, recrystallization, etc.

The compound (III'') is produced by hydrolysis of the compound (III'). The hydrolysis can be effected by any method that is conductive to a cleavage of an amide bond. For example, methods employing an acid, a base or an ion exchange resin may be mentioned. Examples of said acid include inorganic acids such as sulfuric acid and hydrochloric acid and examples of said base include potassium hydroxide, sodium hydroxide and barium hydroxide. Examples of said ion exchange resin include Dowex-50 (Dow Chemical, U.S.A.), Amberlite IR-120 (Rohm and Haas Co., U.S.A.) and Diaison-SK1A and SK1B (Mitsubishi Chemical Industries Ltd., Japan).

When the acid is employed, the reaction is preferably conducted in aqueous solution and when an aqueous solvent is employed, it is preferably a mixture of water with methanol, ethanol, butanol or the like. The reaction is conducted generally at about 60° to 200° C. and preferably at about 90° to 120° C., generally for about 30 minutes to 30 hours and preferably for about 3 to 16 hours.

When the base is employed, the reaction is desirably conducted in aqueous solution. This reaction is also desirably conducted in an aqueous solvent such as a mixture of water with methanol, ethanol, butanol or the like. This reaction is carried out generally at about 60° to 200° C. and preferably at about 90 to 120° C., generally for about 30 minutes to 30 hours and preferably for about 3 to 16 hours.

When the ion exchange resin is employed, the resin is suspended in an aqueous solution of the starting material compound and the suspension is heated. This reaction is conducted generally at 60° to 200° C. and preferably at about 90° to 120° C., generally for about 30 minutes to 30 hours and preferably for about 3 to 16 hours.

Isolation of deacetyl-FA-5859 or a salt thereof from the reaction product mixture can be accomplished by the per se conventional procedures such as ion exchange, adsorption, concentration, crystallization, etc. While the desired compound can be isolated optionally as the free compound or as a salt thereof, it is more expedient to isolate it in the form of a salt.

A typical procedure for isolating the desired substance from the reaction mixture comprises adsorbing the substance on a strongly acidic ion exchange resin or the like, desorbing the same with hydrochloric acid or the like and collecting ninhydrin-positive fractions. When the hydrolysis is effected with hydrochloric acid for instance, a more expedient procedure may be adopted. Thus, the reaction mixture is concentrated under reduced pressure to remove the excess hydrochloric acid and a solvent such as methanol, ethanol or diethyl ether is added to the residue to give hydrochloride of the substance as crystals.

By the process described above is obtained the compound (III) as the free compound or as a salt.

The optically active L form of compound (II), which is the starting compound to be used in practicing the invention is deacetyl-FA-5859. Deacetyl-FA-5859 can be produced, for example, by cultivating a microorganism belonging to the genus Emericella and capable of producing FA-5859 in a culture medium so as to cause formation and accumulation of FA-5859 in the culture medium, collecting the same and subjecting the same to hydrolysis.

The chemical synthesis of the D form of the starting compound (II) for the method according to the invention is as mentioned hereinabove as a method of producing compound (III) from compound (V). As for the L form, it can be produced in the same manner by using the L form of compound (V).

As the microorganism to be used in producing FA-5859 and compound (IV), there may be used, for instance, any microorganisms which belong to the genus Emericella and are capable of producing FA-5859 and/or compound (IV).

As an example of such microorganism, there is mentioned *Emericella quadrilineata*, and more particularly, *Emericella quadrilineata* IFO 5859.

The above-mentioned IFO 5859 strain was deposited on Sept. 14, 1954 at the Institute For Fermentation, Osaka (IFO), Japan, and is listed in the Institute For Fermentation, Osaka (IFO) list of Culomns, 1978, Sixth Edition published by the IFO.

The microbiological characteristics of *Emericella quadrilineata* are as described in Transactions of The Mycological Society of Japan, Volume 20, No. 4, 481 (1979).

As it is true of microorganisms in general, microorganisms of the genus Emericella are liable to undergo mutation whether spontaneously or under the influence of a mutagen. Thus, any and all mutants that are obtainable by irradiation with X-rays, gamma rays, ultraviolet light, etc., monospore separation, treatment with certain reagents or cultivation in media containing such reagents, or other mutagenic treatments, as well as those spontaneous mutants that may be available, can be successfully employed in the production of FA-5859 and/or the compound (IV) when they are still capable of elaborating them.

The medium used for the production of FA-5859 may be liquid or solid, insofar as it contains nutrients available to the strain employed, although a liquid medium is suited for mass production. In the medium are incorporated suitable proportions of assimilable carbon sources, digestable nitrogen sources, inorganic substances and trace nutrients. The carbon sources may for example be glucose, lactose, sucrose, maltose, dextrin, starch, glycerin, mannitol, sorbitol and oils and fats (e.g. soybean oil, olive oil, bran oil, sesame oil, lard oil, chicken oil, etc.), fatty acids (e.g. lauric acid, myristic acid, palmitic acid, stearic acid, oleic acid, etc.). The nitrogen sources may for example be meat extract, yeast extract, dried yeast, soybean flour, corn steep liquor, peptone, cottonseed flour, spent molasses, urea, ammonium salts (e.g. ammonium sulfate, ammonium chloride, ammonium nitrate, ammonium acetate, etc.) and so on. In addition, salts including those of sodium, potassium, calcium, magnesium, etc., metal salts such as those of iron, manganese, zinc, cobalt, nickel, etc., salts of phosphoric acid, boric acid, etc., and salts of organic acids such as acetic acid, propionic acid, etc. are also used as necessary. It is, of course, possible to add amino acids (e.g. glutamic acid, aspartic acid, alaline, lysine, valine, methionine, proline, etc.), peptides (e.g. dipeptides, tripeptides, etc.), vitamins (e.g. $B_1$, $B_2$, nicotinic acid $B_{12}$, C, etc.), nucleic acids (e.g. purine and pyrimidine and their derivatives) and others. Of course, for the purpose of controlling the pH of the medium, an organic or inorganic acid, an alkali, a buffer solution or the like may be added. For defoaming purposes, an oil, a surfactant or the like may also be added to the medium.

The cultural methods that may be employed include stationary culture, shake culture or aerobic submerged or stirred culture, for instance. For mass production, submerged aerobic culture is of course preferable. While the conditions of cultivation, of course, depends on the species or strain of microorganism, the cultural method used and so on, fermentation is generally conducted at a temperature of about 15° to 37° C. with the initial pH being set at pH about 3 to 8. Particularly desirable conditions are about 23° to 32° C. in the intermediate stage of cultivation and pH about 4 to 6 at the start of cultivation. While the cultivation time is also dependent on the abovementioned conditions, it is desirable to continue cultivation until the titer of the physiologically active substance has reached a maximum. In the case of shake culture or submerged aerobic culture in a liquid medium, the duration of time to such maximum titer is generally about 1 to 8 days.

The FA-5859 and the compound (IV) thus elaborated occurs mostly in the liquid phase of the fermentation broth. Therefore, it is a recommend procedure to separate the broth into a supernatant and a cellular mass by filtration or centrifugation and purify the supernatant to recover the desired substance. However, it is also possible to subject the fermentation broth as such directly to a known purification procedure.

To harvest FA-5859 and/or the compound (IV) from the broth, the procedures generally known for the isolation of microbial metabolites can be employed. For example, microbial cells are removed by centrifugation and the active product is separated and purified from the supernatant fluid.

Thus, such procedures as the one utilizing solubilities or a difference in solubility in various solvents, precipitation from a solution, the method utilizing differential rate of precipitation, a difference in adsorptive affinity for a given adsorbent, ion exchange chromatography on ion exchangers, concentration under reduced pressure, crystallization, recrystallization, drying, etc. can be utilized either singly or in a suitable combination or in repetition.

The compound (I), (III) and (IV) each can be converted to a pharmaceutically acceptable salt by the established procedure. As examples of the acid used for this conversion to a salt, there may be mentioned hydrochloric acid, sulfuric acid, nitric acid, oxalic acid, acetic acid, succinic acid, citric acid, fumaric acid, etc.

When the compound (I), (III) and (IV) each is obtained as a salt form, it can be converted to a free form by the established procedure, such as a method employing an ion-exchange resin to absorb the acid or base which forms the salt.

Then, the fatty acid degradation inhibiting activity of the compound (I), (III), (IV) was determined in accordance with the method described in P.75 "Metabolism of Lipids" which is Vol. 9 of "Seikagaku Jikken Koza" (Text of Biochemical Experiments)compiled by Tokyo Kagaku Dojin, published 1975, using rat liver homogenates. Thus, an SD strain rat (6 weeks of age, male) was fasted for one day and, then, bled to death. The liver was immediately excised and homogenized with 10 times (w/v) of a 0.25 M sucrose solution containing a 5 mM Tris-HCl buffer (pH 7.4), 0.1 mM EDTA and 1 mg/ml bovine serum albumin using a Teflon rod homogenizer. The homogenate was centrifuged at 820×g for 10 minutes and the supernatant was further centrifuged at 8,000×g for 10 minutes. The resultant pellets were suspended in the same sucrose solution as above to a concentration of 0.2 g wet liver weight/0.5 ml solution and 0.5 ml of the suspension was used as the enzyme solution in the reaction.

Then, 2.5 ml of a reactant mixture comprising 30 μmole of potassium phosphate buffer (pH 7.4), 300 μmole of KCl, 3 μmole of ATP, 3 μmole of $MgCl_2$, 120 μmole of sucrose, 0.6 μmole of $1-^{14}C$ palmitic acid (0.2 μCi and bovine serum albumin with a molar ratio of 1:5, pH 7.4), 3 μmole of L-carnitine, 0.6 μmole of Coenzyme A, 7.5 μmole of NAD, 0.03 μmole of oxalacetic acid, 0.1 ml of water or an aqueous solution containing an inhibitor and 0.5 ml of the enzyme solution was incubated aerobically at 37° C. for 20 min. in a sealed tube hanging a filter paper immersed with Hyamine Hydroxide 10-X (Packard, Holland) and the reaction was stopped by adding 0.4 ml of 70% perchloric acid. $^{14}CO_2$ formed was trapped and the radioactivity was counted.

The inhibitory activity measured is shown in Table 1. The inhibitory activity is shown as percentages of inhibitory activity to degradation activity of fatty acid facilitated by the addition of carnitine to that of not added of the compound.

TABLE 1

Inhibitory effects derivatives β-amino-γ-trimethylammonio-butyrate on activity of fatty acid degradation which depends on carnitine added.

| Compound (I), (III), (IV) | | Inhibition (%) Concentration of drug | | | |
|---|---|---|---|---|---|
| $R_1$ ($R_2$ = —OH) | Salt | 2 mM | 0.2 mM | 20 μM | 2 μM |
| —COH | | 84 | 53 | | |
| —$COCH_3$(D—) | HCl | 28 | 2 | | |
| —$COCH_2CH_3$ | HCl | 44 | | | |
| —$CO(CH_2)_2CH_3$ | | 50 | | | |
| —$CONH_2$ | HCl | 72 | 34 | | |
| —$COOCH_2C_6H_5$ | | 98 | 85 | | |

TABLE 1-continued

Inhibitory effects derivatives β-amino-γ-trimethylammonio-butyrate on activity of fatty acid degradation which depends on carnitine added.

| | | | | |
|---|---|---|---|---|
| —CO(CH$_2$)$_{14}$CH$_3$ | | | 100 | 100 |
| —H (D—) | 2HCl | 36 | 11 | |
| —CH$_3$ | | 100 | 89 | |

| Compound (I) | | Inhibition % Concentration of drug | | |
|---|---|---|---|---|
| R$_2$ (R$_1$ = H) | Salt | 0.2 mM | 20 µM | 2 µM |
| —OCH$_3$ | 2HCl | | 73 | 26 |
| —OCH$_2$CH$_3$ | 2HCl | | 85 | 37 |
| —O(CH$_2$)$_2$CH$_3$ | 2HCl | | 69 | 41 |
| —NH$_2$ | 2HCl | 67 | 27 | 10 |

Antiketogenic activities of derivatives of β-amino-γ-trimethylammonio-butyrate were measured as follows: After they were fasted for 20 hours, male Sprague-Dawley rats (8 weeks old, n=5) were orally given the compounds which were suspended in 5% gum arabic, at a dose of 50 mg/kg. Blood samples were taken 4 hours later from a vein of tail and ketone bodies were measured as β-hydroxybutyrate according to the modified method of Williamson [D. H. Williamson et al.; Methods of Enzymatic Analysis, P454 (1968), Academic Press, New York]. The amount of ketone bodies was shown as a relative amount of β-hydroxybutyrate (percentage) to the amount of p-hydroxybutyrate in blood of control rats.

Results obtained are shown in Table 2. As seen from the data, good relationship between inhibitory activity of fatty acid degradation and antiketogenic activity of the derivatives of β-amino-γ-trimetylaminobutyrate was observed.

TABLE 2

Antiketogenic activities of derivatives of β-amino-γ-trimethlammoniobutyrate (n = 5)

| Compound (I) , (III), (IV) | | relative amount of |
|---|---|---|
| R$_1$ (R$_2$ = —OH) | Salt | β-hydroxybutylate (%) |
| —COH | | 75.7 |
| —CONH$_2$ | HCl | 63.2 |
| —COOCH$_2$C$_6$H$_5$ | | 19.7 |
| —CO(CH$_2$)$_{14}$CH$_3$ | | 6.7 |
| —CO(CH$_2$)$_{12}$CH$_3$ | | 7.9 |
| —CH$_3$ | | 19.9 |

| Compound (I) | | relative amount of |
|---|---|---|
| R$_2$ (R$_1$ = H) | Salt | β-hydroxybutylate (%) |
| —OCH$_2$CH$_3$ | 2HCl | 5.9 |

In diabetes, blood level of ketone bodies usually increases and so-called ketonemia or ketoacidosis often occurs. This abnormal increase of ketone bodies gives severe damages to patients, such as coma. Consequently, the present compounds, which have antiketogenic activity, are of value as new drugs for the treatment of ketonemia or ketoacidosis.

In particular, it is presumed that the compound (I) wherein R$_1$ is alkyl hardly causes side effect of inducing fatty liver, and that inactivation of the compound by enzymes is decreased. Therefore, the compound (I) wherein R$_1$ is alkyl is advantageously used as a drug.

As shown in Tables 1 and 2, the present compound shows a remarkable fatty acid decomposition inhibitory activity and antiketogenic activity.

Toxicity of the present compound is low, because there is not found dead mouse by 400 mg/kg oral administration.

Therefore, the compounds (I), (III), (IV) or salts thereof is useful as a fatty acid decomposition inhibitor, for instance.

When the compound (I), (III), (IV) or a salt thereof is used as such a fatty acid decomposition inhibitor for the treatment of diabetes in mammalian animals (e.g. mouse, rat, man), it is administered at a daily dose of about 0.2 to 200 mg/kg. The compound (I), (III), (IV) or a salt thereof can be administered orally as such or in combination with a pharmaceutically acceptable carrier, excipient or diluent in such dosage forms as tablets, granules, capsules, liquids, etc., or non-orally in the form of an injectable preparation.

In the production of oral preparations, there may be employed suitable amounts of binders (e.g. hydroxypropyl-cellulose, hydroxypropylmethyl-cellulose, macrogol, etc.), disintegrators (e.g. starch, carboxymethyl-cellulose calcium, etc.), excipients (e.g. lactose, starch, etc.), lubricants (e.g. magnesium stearate, talc, etc.) and so on.

In the production of parenteral or non-oral preparations, e.g. injections, there may be employed isotonicating agents (e.g. glucose, D-sorbitol, D-mannitol, sodium chloride, etc.), preservatives (e.g. benzyl alcohol, chlorobutanol, methyl p-hydroxybenzoate, propyl p-phydroxybenzoate, etc.), buffers (e.g. phosphate buffer, sodium acetate buffer, etc.) and so on.

Figure 1:
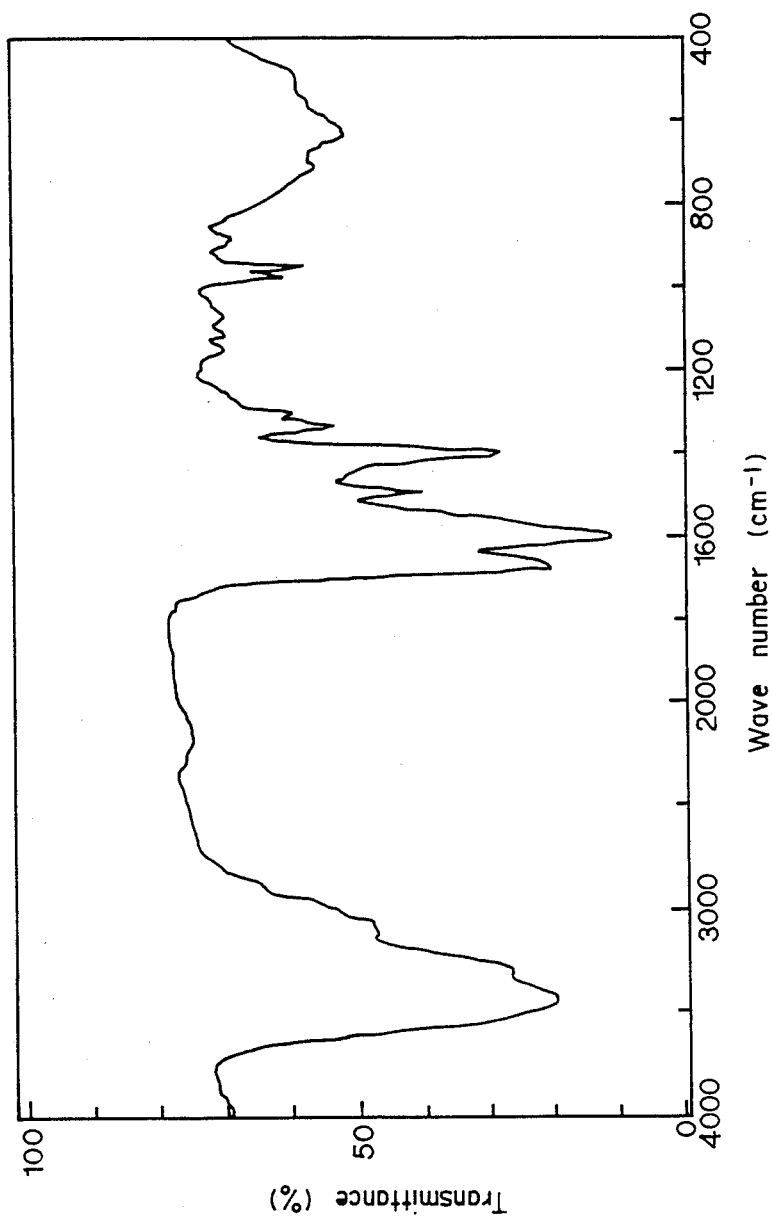
FIG. 1 is an infrared absorption spectrum of physiologically active substance FA-5859 as obtained in Reference Example 2.

The following Reference Examples and Examples are further illustrative of this invention. In the Reference Examples, percent figures with respect to medium compositions are on a weight/volume basis. And in the Examples, the following abbreviations are used.

MeOH: methanol
EtOH: ethanol
AcOEt: acetic acid ethyl ester
A$_2$pr: residue of diaminopropionic acid
A$_2$bu: residue of β,γ-diaminobutyric acid
OMe: methyl ester
Z: benzyloxycarbonyl
BOC: t-butoxycarbonyl
Ac: acetyl

REFERENCE EXAMPLE 1

A loopful of *Emericella quadrilineata* IFO 5859 grown sufficiently to sporulate on a potato-sucrose-agar slant was used to inoculate a 2-liter Sakaguchi flask containing 500 ml of a sterilized medium composed of 2.0% glucose, 3.0% maltose, 1.5% raw soybean flour, 1.0% corn steep liquor, 0.5% Polypepton (Daigo Nutritive Chemicals, Japan), 0.3% yeast extract and 0.3% sodium chloride (pH 6.0), and was incubated on a reciprocating shaker at 28° C. for 2 days. Then, 1.5 l of this seed culture was added to 100 l of a fermentation medium composed of 3.0% oleic acid, 0.5% raw soybean flour, 0.5% malt extract, 0.5% Polypepton, 0.2% yeast extract, 0.1% KH$_2$PO$_4$, 0.05% FeSO$_4$.7H$_2$O, 0.05% MnSO$_4$.nH$_2$O and 0.05% MgSO$_4$.7H$_2$O (pH 4.5) in a 200-l fermentation tank. This fermentation was conducted at 28° C., 100 l/min. aeration, 200 r.p.m. agitation and an internal pressure of 1.0 kg/cm$^2$ for 114 hours. A couple of batches of fermentation thus obtained were pooled and the cells were removed by filtration to give a filtrate containing FA-5859.

REFERENCE EXAMPLE 2

A 125 l portion of the filtrate obtained in Example 1 was passed through a column of Amberlite IR-120 (H+ form) (20 l) and after the column was rinsed with 40 l of water, elution was carried out with b 1N-aqueous ammonia. The eluate was concentrated under reduced pressure to a volume of 30 l to remove the ammonia and the concentrate was passed through a column of chromatographic grade activated carbon (30 l). The column was rinsed with 60 l of water and elution was carried out with 90 l of 50% aqueous methanol. The eluate was collected in 10 l fractions and the active fractions No. 5 to No. 6 were combined and concentrated under reduced pressure to give 25.5 g of a crude syrup. This crude product was dissolved in 100 ml of acetate buffer (pH 4.0) (0.05 M) and the solution was passed through a column of Dowex 50×2 (500 ml) buffered with acetate buffer (0.1 M) (pH 4.0). Then, elution was performed with the same buffer as above in the order of 1 l at pH 4.0, 1.5 l at pH 4.3, 1.5 l at pH 4.6 and 1.5 l at pH 5.0. The eluate was collected in 100 ml fractions and the fractions No. 32 to No. 63 were pooled and passed through a column of Amberlite IR-120 (H+ form) (300 ml). After the column was rinsed with 600 ml of water, elution was carried out with 1.5 l of 0.5N-aqueous ammonia. The eluate was concentrated under reduced pressure to a volume of 500 ml and the concentrate was passed through a column of Dowex 1×2 (OH− form) (200 ml), followed by washing with 200 ml of water. The effluent and washings were combined and concentrated under reduced pressure and lyophilized. Allowing the syrup to stand at room temperature yielded 10.7 g of colorless hygroscopic crystals of FA-5859 (free form). The infrared absorption spectrum of this product is reproduced in FIG. 1.

REFERENCE EXAMPLE 3

Figure 2:
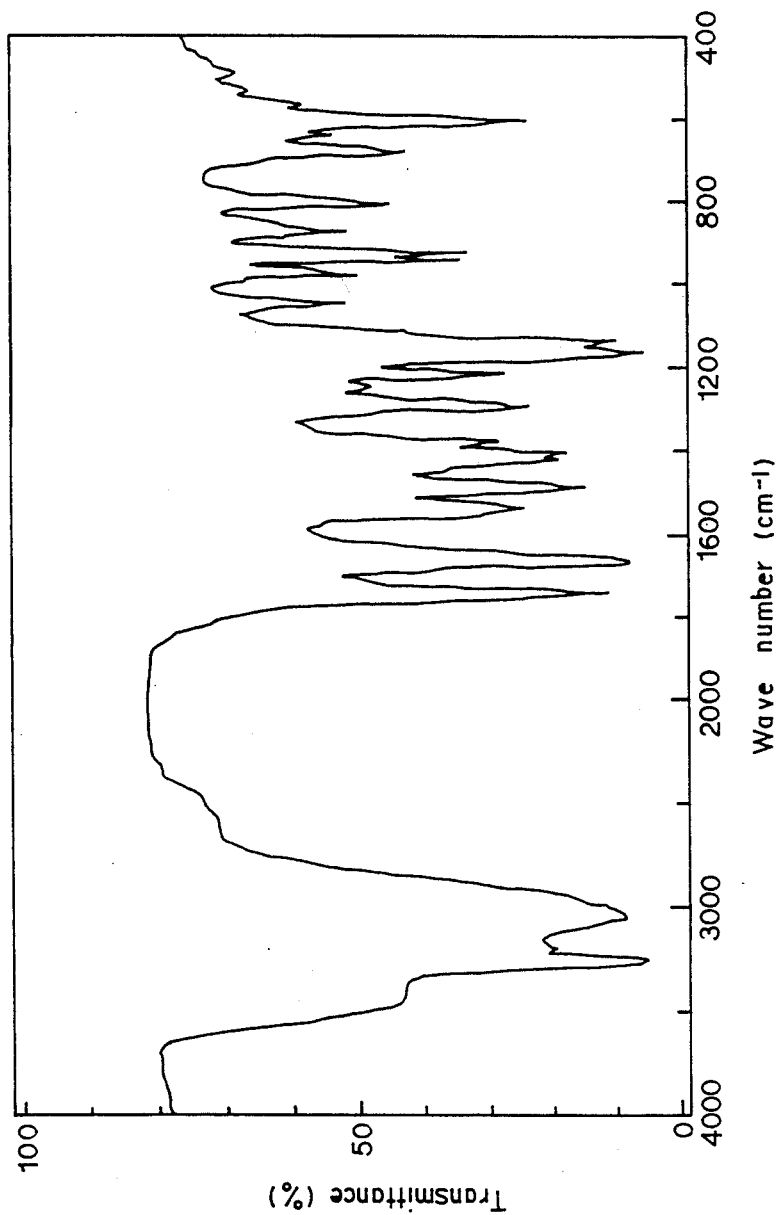
FIG. 2 is an infrared absorption spectrum of the hydrochloride of physiologically active substance FA-5859 as obtained in Reference Example 3.

In 10 ml of water was dissolved 210 mg of FA-5859 free form produced in Reference Example 2, and under ice-cooling, 1 ml of 1N-HCl was added. The mixture was concentrated under reduced pressure and after addition of 10 ml of ethanol, allowed to stand at room temperature. The resultant crystals were recrystallized from water-ethanol to give 225 mg of hydrochloride of FA-5859 as colorless needles. m.p. 215° C. (decompn.). The infrared absorption spectrum of this compound is shown in FIG. 2.

The physico-chemical properties of FA-5859 (free form) as obtained in Refernece Example 2 which appears hereinafter are as follows.

(a) Elemental analysis (%) (after drying over phosphorus pentoxide under reduced pressure at 60° C. for 10 hours)
C: 52.48%
H: 9.04%
N: 13.25%
(b) Molecular weight: $2.4-3.3 \times 10^2$ ($H_2O$) (by VPO method)
(c) Empirical formula: $C_9H_{18}N_2O_3$
(d) Specific rotation: $[\alpha]_D^{23} - 17.4°$ (c=1, $H_2O$)
(e) Ultraviolet absorption spectrum:
No characteristic absorptions at wavelengths over 210 nm.
(f) Infrared absorption spectrum:

Principal absorptions (wave-numbers) are as follows: 3420(s), 3260(sh), 3080(m), 1660(s), 1590(s), 1485(s), 1400(s), 1325(m), 1295(m), 1145(w), 1105(w), 1060(w), 970(m), 945(m), (cm$^{-1}$)
w: weak, m: medium, s: strong, sh: shoulder
Refer to FIG. 1 (potassium bromide disk)
(g) Solubilities:
Insoluble: Petroleum ether, hexane, diethyl ether, benzene, ethyl acetate, chloroform
Hardly soluble: Pyridine, acetone, dimethyl sulfoxide dimethylformamide
Soluble: Ethanol, methanol
Readily soluble: Water
(h) Color reactions
Positive: Iodine reaction
Negative: Greig-Leaback, ninhydrin, Sakaguchi, Molisch and Ehrlich reactions
(i) Basic, acidic or neutral: Amphoteric
(j) Color of the substance: Colorless
(k) Appearance of crystals: Colorless hygroscopic crystals
(l) Nuclear magnetic resonance spectrum (CD$_3$OD, 100 MHz): 1.98(3H,s), 2.42(2H,d), 3.19(9H,s), 3.56(2H,d), 4.7(1H,m)
s: singlet, d: doublet, m: multiplet
(m) Stability: Stable in aqueous solution at pH 3 to 9 under heating at 100° C. for 10 minutes.

The physico-chemical properties of FA-5859. hydrochloride as obtained in Reference Example 3 which appears hereinafter are as follows:
(a) Elemental analysis (%): (after drying under reduced pressure over phosphorus pentoxide at 60° C. for 10 hours)
C: 45.29%
H: 8.18%
N: 11.24%
Cl: 14.36%
(b) Empirical formula: $C_9H_{18}N_2O_3 \cdot HCl$
(c) Melting point 215° C. (decompn.)
(d) Specific rotation: $[\alpha]_D^{23} - 20.5°$ (c=1, $H_2O$)
(e) Ultraviolet absorption spectrum:
No characteristic absorptions at wavelengths over 210 nm.
(f) Infrared absorption spectrum:
Dominant absorptions (wave-numbers) are as follows. 3400(m), 3250(s), 3190(sh), 3045(s), 2600–2400(w), 1730(s), 1660(s), 1530(m), 1480(s), 1420(m), 1405(s), 1375(m), 1290(m), 1205(m), 1160(s), 1140(sh), 1135(s), 1040(w), 960(w), 935(m), 915(m), 865(w), 800(m), 665(m), 625(w), 600(s), 560(w) (cm$^{-1}$)
(w: weak, m: medium, s: strong)
Refer to FIG. 2 (potassium bromide disc)
(g) Solubilities
Insoluble: petroleum ether, hexane, diethyl ether, benzene, ethyl acetate, chloroform
Hardly soluble: pyridine, acetone, dimethyl sulfoxide, dimethylformamide
Soluble: ethanol, methanol
Readily soluble: water
(h) Color reactions:
Positive: iodine reaction
Negative: Greig-Leaback, ninhydrin, Sakaguchi, Molisch and Ehrlich reactions
(i) Color of the substance: colorless
(j) Appearance of crystals: colorless needles
(k) Stability: Aqueous solutions at pH 3 to 9 are stable at 100° C. for 10 minutes.

The molecular formula of FA-5859 and the NMR signal at δ 3.19 ppm (9H, s) suggest the presence of a trimethylammonium group in the molecule. Moreover, the NMR spectrum indicates the presence of methyl protons of the acetyl group (CH₃CO—) at a 1.98 ppm (3H, s) and a couple of methylene protons (—CH₂—×2) at δ 2.42 ppm (2H, d) and 3.56 ppm (2H, d) and a methine proton

δ 4.7 ppm. Decoupling studies reveal that the above couple of methylene protons are respectively coupled with the methine proton at δ 4.7 ppm, suggesting the existence of a partial structure of

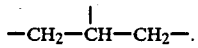

Moroever, the molecular formula of this compound suggests the presence of a carboxyl group. This is also apparent from the fact that a C=O vibration is seen at 1590 cm$^{-1}$ in the case of the free compound and at 1730 cm$^{-1}$ in the case of the hydrochloride.

Therefore, the following planar structural formula may be advanced for FA-5859.

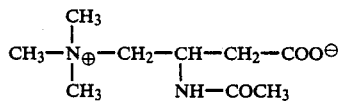

FA-5859 is in the optically active L form, because of its specific rotation. The salts is also L-form.

REFERENCE EXAMPLE 4

In 40 ml of constant boiling point hydrochloric acid was dissolved 1.60 g of free FA-5859 obtained in Reference Example 2 and the solution was allowed to stand at 95° C. for 16 hours. The reaction mixture was concentrated under reduced pressure and the residue was diluted with a small amount of water and concentrated under reduced pressure for a second time. To the residue was added a mixture of methanol and diethyl ether and the resultant crystals were collected by filtration. Recrystallization from methanol gave 1.20 g of deacetyl-FA-5859.2HCl. m.p. 219°–220° C.; $[\alpha]_D^{22}+6.3°$ (c=1.0, 1N-AcOH).

Elemental analysis: $C_7H_{18}O_2N_2Cl_2$ Calcd.: C, 36.05; H, 7.77; N, 12.01; Cl, 30.40(%), Found : C, 36.09; H, 7.72; N, 11.81; Cl, 29.80(%). Absorption spectrum: No characteristic absorption over the ultraviolet and visible region from 210 nm to 700 nm.

The product is assumed to be in the optically active L-form, because of its specific rotation.

EXAMPLE 1

Production of [(R)-3-carboxy-2-formylaminopropyl]-trimethylammonium picrate:

A solution of 930 mg of deacetyl-FA-5859 dihydrochloride obtained in Reference Example 4 (the same was used in Examples 1 to 12 and 14)in 10 ml of formic acid was cooled to 0° C., and 336 mg of NaHCO₃ and 2.8 ml of acetic anhydride were added. The mixture was stirred for an hour and then at room temperature for 4 further hours. The reaction mixture was cooled, and 50 ml of water was added. After solvent removal by distillation under reduced pressure, the residue was dissolved in 100 ml of water and the solution was passed through a Dowex 50W×2 column (H⁺ form; 80 ml). After washing the column with 300 ml of water, elution was performed with 0.5 N aqueous ammonia. The eluate was evaporated under reduced pressure to remove the solvent and the residue, which weighed 880 mg, was dissolved in 10 ml of methanol. To the solution was added a solution of 1.10 g of picric acid in 30 ml of ethanol, and the resulting precipitate was collected by filtration. Recrystallization from methanol gave 1.25 g of the title compound.

Melting point: 174°–176° C., $[\alpha]_D^{24}-3.3°$ (c=1.0, dimethylformamide).

Elemental analysis: Calcd. for $C_{14}H_{19}N_5O_{10}$: C, 40.29; H, 4.59; N, 16.78%; Found: C, 40.18; H, 4.64; N, 16.75%.

EXAMPLE 2

Production of [(R)-3-carboxy-2-propionylaminopropyl]trimethylammonium chloride:

A solution of 700 mg of deacetyl-FA-5859 dihydrochloride in 20 ml of water was cooled to 0° C., and 1.10 g of NaHCO₃, 20 ml of acetonitrile and 0.58 ml of propionic anhydride were added. The mixture was stirred at 0° C. for an hour and then further at room temperature for 5 hours. The acetonitrile was distilled off and 100 ml of water was added. The mixture was passed through a Dowex 50 W×2 column (H⁺ form; 80 ml). After washing the column with 240 ml of water, elution was performed with 0.5 N ammonia water. The eluate was evaporated under reduced pressure to remove the solvent and the residue (0.63 g) was dissolved 2.8 ml of 1 N HCl. After removal of the water by distillation, the residue was treated with methanol-ethyl ether to give 0.59 g of the title compound as colorless crystals.

Melting point: 161°–163° C., $[\alpha]_D^{24}-16.7°$ (c=1.0, water)

Elemental analysis: Calcd. for $C_{10}H_{21}N_2O_3Cl$: C, 47.52; H, 8.37; N, 11.08; Cl, 14.03%; Found: C, 47 18; H, 8.40; N, 10.90; Cl, 13.88%.

EXAMPLE 3

Production of [(R)-3-carboxy-2-n-butyrylaminopropyl]-trimethylammonium picrate:

A solution of 700 mg of deacetyl-FA-5859 dihydrochloride in 20 ml of water was cooled, and 1.10 g of NaHCO₃, 20 ml of acetonitrile and 0.7 ml of n-butyric anhydride were added. The mixture was stirred at 0° C. for an hour and then at room temperature for an additional 6 hours. The acetonitrile was distilled off and the residue was dissolved in 100 ml of water. The solution was passed through a Dowex 50 W×2 column (H⁺ form; 80 ml). After washing the column with 300 ml of water, elution was performed with 0.5 N aqueous ammonia. The eluate was evaporated under reduced pressure to remove the solvent and the resulting oily product (0.65 g) was dissolved in 10 ml of methanol, followed by addition of a solution of 1.0 g of picric acid in 40 ml of ethanol. The resulting crystalline precipitate was collected by filtration and recrystallized from ethanol to give 0.91 g of the title compound.

Melting point: 176°–177° C., $[\alpha]_D^{24}-0.9°$ (c=1.0, dimethylformamide).

Elemental analysis: Calcd. for $C_{17}H_{25}N_5O_{10}$: C, 44.44; H, 5.49; N, 15.29%; Found: C, 44.22; H, 5.22; N, 15.30%.

EXAMPLE 4

Production of (R)-3-palmitoylamino-4-trimethylammoniobutyrate:

A solution of 446 mg of deacetyl-FA-5859 dihydrochloride in 20 ml of water was cooled, and 8 ml of 1 N NaOH and 20 ml of acetonitrile were added, followed by drop-wise addition of 550 mg of palmitoyl chloride with stirring. The mixture was stirred at 0° C. for one hour and then at room temperature for an addition 10 hours and the insoluble matter was filtered off, followed by removal of the acetonitrile by distillation under reduced pressure. The residue was acidified with 1 N HCl and extracted with n-butanol (50 ml×2). After removal of the n-butanol by distillation under reduced pressure, the residue was dissolved in a small amount of water and the insoluble matter was filtered off. The filtrate was lyophilized to give 105 mg of a colorless powder. This powder (90 mg) was dissolved in 10 ml of 5% (v/v) n-butanol-water and the solution was passed through a column of Amberlite IRA-402 (Rohm and Haas Company, U.S.A.) (acetic acid form, 5 ml). The effluent and aqueous washings were combined, concentrated and lyophilized to give 81 mg of the dihydrate of the title compound.

$[\alpha]_D^{24} -11.2°$ (c=0.5, MeOH)

Elemental analysis: Calcd. for $C_{23}H_{46}N_2O_3 \cdot 2H_2O$: C, 63.55; H, 11.59; N, 6.44%; Found: C, 63.82; H, 11.10; N, 6.13%.

EXAMPLE 5

Production of [(R)-3-carboxy-2-methoxycarbonylaminopropyl]trimethylammonium chloride:

To a cooled solution of 816 mg of deacetyl-FA-5859 dihydrochloride in 20 ml of water, there were added 1.29 g of $NaHCO_3$ and 395 mg of methoxycarbonyl chloride. The mixture was stirred at 0° C. for 30 minutes and then at room temperature overnight. The reaction mixture was neutralized with 1 N HCl and then washed with 50 ml of AcOEt. The aqueous layer was chromatographed on a Dowex 50 W×2 column ($H^+$ form, 100 ml). After washing the column with 400 ml of water, elution was effected with 0.5 N aqueous ammonia. The eluate was concentrated under reduced pressure, and the residue was dissolved in 30 ml of water. The solution was passed through an Amberlite IRC-50 column ($H^+$ form, 10 ml). The column was washed with 200 ml of water. The effluent and washings were combined and evaporated under reduced pressure. The oil (0.75 g) thus obtained was dissolved in 3 ml of 1 N HCl, followed by evaporation again under reduced pressure. Crystallization of the residue by addition of ethyl ether gave 0.65 of the title compound.

Melting point: 201°–205° C. (decomposition)

$[\alpha]_D^{25} -22.3°$ (c=0.75, water)

Elemental analysis:

Calcd. for $C_9H_{19}N_2O_4Cl$: C, 42.43; H, 7.52; N, 10.99; Cl, 13.92%; Found: C, 42.10; H, 7.23; N, 10.64; Cl, 13.84%.

EXAMPLE 6

Production of (R)-3-benzyloxycarbonylamino-4-trimethylammoniobutyrate:

To a cooled solution of 1.63 g of deacetyl-FA-5859 dihydrochloride in 28 ml of 1 N NaOH, there were added 5 ml of acetonitrile and 1.70 g of benzyloxycarbonyl chloride. The mixture was stirred vigorously at 0° C. for 2 hours, followed by further stirring at room temperature for 12 hours. The reaction mixture was washed with 50 ml of ethyl ether, and the aqueous layer was chromatographed on a Dowex 50 W×2 column ($H^+$ form, 150 ml). After washing with 300 ml of water, elution was effected with 0.5 N aqueous ammonia. The eluate was evaporated under reduced pressure, and the residue was dissolved in 30 ml of water. The solution was extracted with n-butanol (100 ml×3), the n-butanol was then distilled off under reduced pressure, and the resulting crystals were collected and recrystallized from n-propanol-ethyl ether to give 0.90 g of the title compound.

Melting point: 196°–197° C.

$[\alpha]_D^{21} -19.8°$ (c=0.51, water)

Elemental analysis:

Calcd. for $C_{15}H_{22}N_2O_4$: C, 61.20; H, 7.53; N, 9.52%; Found: C, 61.04; H, 7.71; N, 9.51%.

EXAMPLE 7

Production of [(R)-3-carboxy-2-carbamoylaminopropyl]trimethylammonium chloride:

Potassium cyanide (364 mg) was added to a solution of 700 mg of deacetyl-FA-5859 dihydrochloride in 20 ml of water. The mixture was allowed to stand at room temperature for 12 hours. The reaction mixture was chromatographed on a Dowex 50 W×2 column ($H^+$ form, 80 ml), followed by washing with 240 ml of water and elution with 0.5 N aqueous ammonia. The eluate was evaporated under reduced pressure, the residue was dissolved in 3 ml of 1 N HCl and the water was distilled off under reduced pressure. The oil thus obtained was crystallized from MeOH-ethyl ether and recrystallized from MeOH-EtOH to give 0.53 g of the title compound.

Melting point: 215°–217° C. (decomposition)

$[\alpha]_D^{25} -24.1°$ (c=1, water)

Elemental analysis:

Calcd. for $C_8H_{18}N_3O_3Cl$: C, 40.07; H, 7.56; N, 17.52; Cl, 14.80%; Found: C, 40.04; H, 7.55; N, 17.14; Cl, 14.87%.

EXAMPLE 8

Production of [(R)-2-ammonia-3-carbomethoxypropyl]trimethylammonium dipicrate:

To a suspension of 1.0 g of deacetyl-FA-5859 dihydrochloride in 20 ml of MeOH, there was added 5 ml of 6 N NCl-MeOH, and the mixture was allowed to stand at room temperature for 2 days. The MeOH was then distilled off under reduced pressure, the residue was dissolved in 50 ml of MeOH, a solution of 2.0 g of picric acid in 50 ml of ethanol was added, and the resulting crystalline precipitate was collected by filtration. Recrystallization from MeOH gave 1.60 g of the title dipicrate.

Melting point: 139°–140° C.

$[\alpha]_D^{24} -7°$ (c=1.0, dimethylformamide)

Elemental analysis:

Calcd. for $C_{20}H_{24}N_8O_{16}$: C, 37.98; H, 3.82; N, 17.71%; Found: C, 37.81; H, 4.04; N, 17.45%.

EXAMPLE 9

Production of [(R)-2-ammonio-3-carboethoxypropyl]trimethylammonium monochloride monopicrate:

EtOH (10 ml) was cooled to −20° C. and 0.4 ml of thionyl chloride was added dropwise, followed by addition of 0.92 g of deacetyl-FA-5859 dihydrochloride. The mixture was stirred at 0° C. for an hour and then at 60° C. for 8 hours. After removal of the EtOH by distillation under reduced pressure, the residue was dissolved in 10 ml of EtOH and a solution of 2.0 g of picric acid in 50 ml of EtOH was added. The resulting crystalline precipitate was collected by filtration and recrystallized from MeOH-EtOH to give 1.20 g of the title compound.

Melting point: 204°–208° C.

$[\alpha]_D^{25} -2.8°$ (c=1.1, dimethylformamide)

Elemental analysis: Calcd. for $C_{15}H_{24}N_5O_9Cl$: C, 39.69; H, 5.32; N, 15.43; Cl, 7.82%; Found: C, 39.44; H, 4.90; N, 15.43; Cl, 7.09%.

EXAMPLE 10

Production of [(R)-2-ammonio-3-carbopropoxypropyl]-trimethylammonium dipicrate:

N-Propanol (20 ml) was cooled to −20° C. and 0.4 ml of thionyl chloride was added dropwise, followed by addition of 0.70 g of deacetyl-FA-5859 dihydrochloride. The mixture was stirred at 0° C. for an hour and then at 60° C. for 24 hours. After removal of the n-propanol by distillation under reduced pressure, the residue was dissolved in 10 ml of n-propanol and a solution of 0.9 g of picric acid in 20 ml of EtOH was added. The resulting crystalline precipitate was collected by filtration and recrystallized from MeOH-EtOH to give 1.0 g of the title dipicrate.

Melting point: 109°–111° C.

$[\alpha]_D^{25} =0.4°$ (c=0.93, dimethylformamide)

Elemental analysis: Calcd. for $C_{22}H_{28}N_8O_{16}$: C, 40.00; H, 4.27; N, 16.96%; Found: C, 39.73; H, 4.32; N, 16.76%.

EXAMPLE 11

Production of [(R)-2-ammonio-3-carbamoylpropyl]-trimethylammonium dipicrate:

MeOH (20 ml) was cooled to −20° C. and 0.4 ml of thionyl chloride was added dropwise with stirring, followed by addition of 1.30 g of deacetyl-FA-5859 dihydrochloride. The mixture was stirred at 0° C. for an hour and then at 60° C. for 3 hours. After removal of the MeOH by distillation under reduced pressure, the residue was dissolved in 10 ml of MeOH and a solution of 2.0 g of picric acid in 30 ml of MeOH was added. The resulting crystalline precipitate was collected by filtration to give crystals (2.20 g), which was recrystallized from MeOH, giving 1.80 g of [(R)-2-ammonio-3-carbomethoxypropyl]trimethylammonium dipicrate. This product (1.0 g) was dissolved in 20 ml of MeOH, and 10 ml of 15 N ammonia water was added. The mixture was allowed to stand at room temperature for 2 days and evaporated under reduced pressure. To the residue was added EtOH and the resulting crystalline precipitate was collected by filtration and recrystallized from MeOH-water to give 0.65 g of the title compound.

Melting point: 226°–227° C.

$[\alpha]_D^{25} +2.9°$ (c=1.0, dimethylformamide)

Elemental analysis: Calcd. for $C_{19}H_{23}N_9O_{15}$: C, 36.96; H, 3.75; N, 20.42%; Found: C, 36.99; H, 3.73; N, 20.44%.

EXAMPLE 12

Production of (R)-3-myristoylamino-4-trimethylammoniobutyrate:

Using 466 g of deacetyl-FA-5859 dihydrochloride and 520 mg of myristoyl chloride and following the procedure of Example 4 for the production of the palmitoyl compound, there was obtained 110 mg of the title compound $^1$H-NMR (in $CD_3OD$) δ ppm: 0.85(3H, t, —$CH_3$), 1.27(20H, m, —$(CH_2)_{10}$—$CH_3$), 3.15(9H, s, $(CH_3)_3N^+$—), 3.52(2H, d, —$CH_2$—$^+N(CH_3)_3$)

EXAMPLE 13

Production of [(R)-2-caprylamino-3-carbomethoxypropyl]trimethylammonium chloride:

[(R)-2-Ammonio-3-carbomethoxypropyl]trimethylammonium dipicrate (500 mg) as obtained in Example 8 was dissolved in dimethylformamide (4 ml), and triethylamine (0.6 ml) and a solution of capryl chloride (528 mg) in dimethylformamide (4 ml) were serially added to the solution. The mixture was stirred at room temperature for 3 hours and the solvent was then distilled off under reduced pressure. To the residue was added water (50 ml) and the mixture was adjusted to pH 2 with 1 N hydrochloric acid and extracted with ether (30 ml×5). The ether layers were combined and extracted with water (100 ml×3). The aqueous layer was adjusted to pH 11 with 1 N sodium hydroxide and extracted with ethyl acetate-ether (1:1) (150 ml×2). The extract was washed with water and the solvent was distilled off. The residue was dissolved in 20% methanol-water (50 ml) and passed through an IBA-402 column (Cl form; 5 ml). The effluent and 20% methanol-water washings (20 ml) were combined and lyophilized to give a hygroscopic powder (40 mg).

IR $\nu_{max}^{KBr}$ cm$^{-1}$: 2930, 2860, 1750, 1665

$^1$H-NMR δ ppm (in heavy water) 0.88(3H, t, $CH_3$—$(CH_2)_6$—), 1.30(12H, $CH_3$—$(CH_2)_6$—), 1.63 (2H, m, —$(CH_2)_6$—$CH_2$—), 2.30(2H, t, —$CH_2$—CONH—), 2.81(2H, —$CH_2$—$COOCH_3$), 3.27(9H, s, $(CH_3)_3^{\oplus}N$—), 3.73(3H, s, —$COOCH_3$)

EXAMPLE 14

Production of (R)-3-benzoylamino-4-trimethylammoniobutyrate:

To a solution of 700 mg of deacetyl-FA-5859 dihydrochloride in 20 ml of water were added 20 ml of acetonitrile, 1.0 g of benzoic anhydride and 1.1 g of $NaHCO_3$, and the mixture was stirred at 0° C. for an hour and then at room temperature for 5 hours. The solvent was then distilled off and the residue was acidified with 1 N aqueous hydrochloric acid and washed with ether. The aqueous layer was passed through a Dawex 50 W×2 column (H$^+$ form; 80 ml). After washing the column with 200 ml of water, elution was performed with 0.5 N aqueous ammonia. The eluate was evaporated under reduced pressure and the residue was dissolved in water, followed by lyophilization to give 450 mg of the title compound $^1$H-NMR δ ppm(in heavy water): 2.65(2H, d, —$CH_2$—COO—), 3.24(9H, s, $(CH_3)N^+$—), 3.70(2H, q, $(CH_3)_3N^+$—$CH_2$—), 7.70

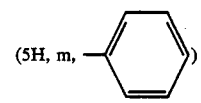

(5H, m, )

EXAMPLE 15

Production of [(R)-2-benzoylamino-3-carbomethoxypropyl]trimethylammonium chloride:

MeOH (10 ml) was cooled to −20° C. and, with stirring, 0.15 ml of thionyl chloride was added. To the mixture was added 300 mg of (R)-benzoylamino-4-trimethylammoniobutyrate as obtained in Example 14, and the whole mixture was stirred at 0° C. for an hour and then at room temperature for 10 hours. After removal of the solvent by distillation, the residue was dissolved in 50 ml of 10% MeOH-water and the solution was passed through an Amberlite IRA-402 column (Cl− form; 5 ml). The effluent and 10% MeOH washings were combined and evaporated under reduced pressure, and the residue was dissolved in water, followed by lyophilization to give 250 mg of the title compound as a hygroscopic powder.

1H-NMR δ ppm(in heavy water): 2.86(2H, d, —CH$_2$—COOCH$_3$), 3.25(9H, s, (CH$_3$)N$^+$—), 3.72(3H, s, —COOCH$_3$), 7.70

(5H, m, 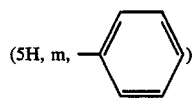)

EXAMPLE 16

Production of (S)-2-acetylamino-3-carboxypropyl)-trimethylammonium chloride:

(1) Production of Z—D—A$_2$Pr—OH

In a mixture of dimethylformamide and water (50 ml-50 ml) was dissolved 12.9 g of bistrifluoroacetoxyphenyliodine and the solution was stirred vigorously. After 15 minutes, 3.2 ml of pyridine was added and the mixture was stirred at room temperature for 4 hours. The solvent was then distilled off under reduced pressure and the resulting crystalline precipitate was collected by filtration. Recrystallization from EtOH gave 3.5 g of Z—D—A$_2$pr—OH.

Melting point: 227°–228° C.

$[\alpha]_D^{24}$ +8.8° (c=0.4, 1 N NaOH)

Elemental analysis: Calcd. for C$_{11}$H$_{14}$N$_2$O$_4$: C, 55.44; H, 5.92; N, 11.76%; Found: C, 54.96; H, 5.76; N, 11.30%.

(2) Production of Z—D—A$_2$pr(POC)—OH

In a mixture of water and acetonitrile was suspended 3,3 g of Z—D—A$_2$pr—OH and the suspension was cooled to 0° C., followed by dropwise addition of 4 ml of triethylamine. To the mixture was added 4.1 g of 2-t-butoxycarbonyloxyimino-2-phenylacetonitrile (BOC-ON), and the whole mixture was stirred at room temperature overnight. The solvent was then distilled off and the residue was washed with ml of ether. The aqueous layer was acidified with 10% aqueous citric acid and extracted with 100 ml of AcOEt. The extract was washed with water and dried over anhydrous Na$_2$SO$_4$. The AcOEt was distilled off and the residue was crystallized from petroleum ether. Yield 2.90 g.

Melting point: 142°–143° C.

$[\alpha]_D^{25}$ +11.0° (c=0.5, methanol)

Elemental analysis: Calcd. for C$_{16}$H$_{22}$N$_2$O$_6$: C, 56.79; H, 6.55; N, 8.28%; Found: C, 56.77; H, 6.66; N, 8.04%.

(3) Production of Z—D—A$_2$bu(BOC)—OMe

A solution of 2.80 g of Z—D—A$_2$pr(BOC)—OH and 0.92 ml of N-methylmorpholine in 60 ml of AcOEt was cooled to −10° C., and 1.10 ml of ethyl chlorocarbonate was added. The mixture was stirred at 0° C. for 30 minutes. The insoluble matter was filtered off and a diazomethane-ethyl ether solution was added in excess to the filtrate. The mixture was stirred at 0° C. for an hour and then at room temperature overnight. The solvent was then distilled off under reduced pressure and the residue was dissolved in 50 ml of MeOH, followed by addition of a solution of 100 mg of silver benzoate in 1 ml of triethylamine. The mixture was stirred in the dark for 4 hours. The insoluble matter was filtered off and the filtrate was concentrated under reduced pressure The residue was extracted with 200 ml of AcOEt. The AcOEt extract was washed with 10% aqueous citric acid, 5% aqueous NaHCO$_3$ and water in that order and dried over anhydrous Na$_2$SO$_4$. The AcOEt was distilled off and the resulting crystalline precipitate was collected by filtration and recrystallized from AcOEt-petroleum benzine. Yield 1.50 g.

Melting point: 101°–103° C.

$[\alpha]_D^{24}$ −5.6° (c=0.9, dimethylformamide)

Elemental analysis:

Calcd. for C$_{18}$H$_{26}$N$_2$O$_6$: C, 59.00; H, 7.15; N, 7.65%; Found: C, 59.13; H, 7.06; N, 7.60%.

(4) Production of Z—D—A$_2$bu(BOC)—OH

A solution of 1.45 g of Z—D—A$_2$bu(BOC)—OMe in 30 ml of MeOH was cooled to 0° C. and 6 ml of 1 N NaOH was added dropwise to the solution. The mixture was stirred at room temperature for 2 hours and the MeOH was distilled off under reduced pressure. The residue was acidified with 10% aqueous citric acid and extracted with 100 ml of AcOEt. The extract was washed with water and dried over anhydrous Na$_2$SO$_4$. The AcOEt was then distilled off and petroleum benzine was added to the residue. The crystals thus obtained were recrystallized from AcOEt-petroleum benzine. Yield 1.15 g.

Melting point: 136°–137° C.

$[\alpha]_D^{24}$ −12.0° C. (c=1.0, dimethylformamide)

Elemental analysis: Calcd. for C$_{17}$H$_{24}$N$_2$O$_6$: C, 57.94; H, 6.87; N, 7.95%; Found: C, 58.25; H, 6.75; N, 7.78%.

(5) Production of Ac—D—A$_2$bu(BOC)—OH

In 10% MeOH-water (v/v) was dissolved 1.10 g of Z—D—A$_2$—bu(BOC)—OH and catalytic reduction was carried out in the presence of palladium black. The catalyst was then filtered off and the filtrate was concentrated under reduced pressure. The residue was dissolved in a water-dioxane (20 ml-20 ml) mixture, and 0.80 ml of triethylamine and 0.80 g of N-acetyloxy-5-norbornene-2,3-dicarboximide were added. The mixture was stirred at room temperature for 5 hours. The dioxane was distilled off and the residue was washed with 50 ml of AcOEt. The aqueous layer was acidified with 10% aqueous citric acid and extracted with AcOEt (100 ml×2). The AcOEt layer was washed with 5% aqueous sodium chloride and dried over anhydrous Na$_2$SO$_4$. The AcOEt was then distilled off and the residue was crystallized from petroleum benzine, followed by recrystallization from AcOEt. Yield 0.57 g.

Melting point: 139°–140° C.

$[\alpha]_D^{24}$ −25.4° (c=0.80, dimethylformamide)

Elemental analysis: Calcd. for C$_{11}$H$_{20}$N$_2$O$_5$: C, 50.75; H, 7.75; N, 10.76%; Found: C, 51.11; H, 7.43; N, 10.79%.

(6) Production of [(S)-2-acetylamino-3-carboxypropyl]trimethylammonium chloride

In 20 ml of trifluoroacetic acid was dissolved 0.53 g of Ac—D—A$_2$bu(BOC)—OH and the solution was allowed to stand at room temperature for 15 minutes. The trifluoroacetic acid was distilled off. Upon treatment with ether, the residue turned into a powder. This powder was dissolved in 8 ml of 8% aqueous NaOH and the solution was cooled to 0° C., followed by dropwise addition of 0.5 ml of dimethyl sulfate. The mixture was stirred vigorously at 0° C. for 30 minutes and then at room temperature for 3 hours, diluted with 100 ml of water and passed through a Dowex 50 W×2 column (H+ form, 100 ml). After washing the column with 300 ml of water, elution was carried out with 0.5 N aqueous ammonia. The eluate was evaporated under reduced pressure to remove the solvent and the residue was dissolved in 3 ml of 1N HCl, followed by concentration under reduced pressure. The resulting oily product was crystallized from MeOH-ethyl ether to give 415 mg of the title compound.

Melting point: 218°-220° C.

$[\alpha]_D^{24} +20.5°$ (c=0.92, water)

Elemental analysis: Calcd. for $C_9H_{19}N_2O_3Cl$: C, 45.28; H, 8.02; N, 11.73; Cl, 14.85%; Found: C, 45.20; H, 8.10; N, 11.47; Cl, 14.85%.

EXAMPLE 17

Production of [(S)-2-ammonio-3-carboxypropyl]trimethylammonium dichloride:

[(S)-2-Acetylamino-3-carboxypropyl]trimethylammonium chloride (205 mg) as obtained in Example 16 was dissolved in 10 ml of 5.5 N HCl and treated with at 100° C. for 10 hours. The reaction mixture was concentrated under reduced pressure and the residue was crystallized from MeOH-ethyl ether. Yield 173 mg.

Melting point: 214°-216° C. (decomposition)

$[\alpha]_D^{24} -8.2°$ (c=0.58, water)

Elemental analysis: Calcd. for $C_7H_{18}N_2O_2Cl_2$: C, 36.05; H, 7.77; N, 12.01; Cl, 30.40%; Found: C, 35.94; H, 7.61; N, 12.14; Cl, 28.92%.

EXAMPLE 18

(1) The lyophilizate (8.0 g) obtained in the manner as Reference Examples 1 and 2 was recrystallized twice from ethyl alcohol-ethyl ether. The mother liquor was evaporated under reduced pressure and the resulting oil was subjected to column chromatography using Dowex 50 W×8 (100-200 mesh, 400 ml). Elution was carried out with 0.05M citric acid buffer and the 5.7-6.2 l eluate fractions were combined and passed through a Dowex 50 W×2 column (100 ml, H+ form) After washing the column with 300 ml of water, elution was carried out with 0.5 N aqueous ammonia. The eluate was concentrated and the resulting oil was dissolved in methanol, followed by addition of a 5% picric acid-ethanol solution. The resulting crystalline precipitate was collected by filtration and recrystallized from methanol to give 210 mg of [(R)-3-carboxy-2-propylaminopropionyl]trimethylammonium picrate.

Elemental analysis: Calcd. for $C_{16}H_{23}N_5O_{15}$: C, 43.15; H, 5.20; N, 15.72%; Found: C, 43.32; H, 5.27; N, 15.69%.

(2) The 6.4-6.8 l eluate fractions obtained in the above Dowex 50 W×8 (100-200 mesh) column chromatography were combined, desalted with Dowex 50 W×2 (H+ form) in the same manner as above, and crystallized using picric acid. There was thus obtained 95 mg of [(R)-3-carboxy-2-butyrylaminopropyl]trimethylammonium picrate.

Elemental analysis: Calcd. for $C_{17}H_{25}N_5O_{10}$: C, H, 5.48; N, 15.24%; Found: C, 44.38; H, 5.43; N, 15.30%.

EXAMPLE 19

Production of [(R)-2-methylammonio-3-carboxypropyl]trimethylammonium . dichloride:

(1) Production of (R)-3-(N-acetyl-N-methylamino)-4-trimethylammoniobutyrate:

In 40 ml of dimethylformamide were dissolved 1.9 g of FA-5859 hydrochloride obtained in the manner of Reference Example 3 and 7.0 g of silver oxide; and then 4.0 ml of methyl iodide was added to the mixture under stirring. The reaction mixture was stirred at 45° C. for 5 hours, and the insolubles were removed by filtration. Dimethylformamide was removed by evaporation under reduced pressure, and to the residue were added 20 ml of methanol and 30 ml of 1N aqueous sodium chloride. Insolubles were removed by filtration and the filtrate was stirred for 2 hours at room temperature.

After methanol was removed by evaporation, the residue was dissolved in 100 ml of water and the solution was passed through a Dowex 50 W×2 column (H+ form; 100 ml).

After washing the column with 300 ml of water, elution was performed with 400 ml of 0.5N-aqueous ammonia. The eluate was subjected to evaporation to remove the solvent, and the oily residue, which was 1.6 g, was dissolved in 20 ml of water. The solution was passed through a CM-Sephadex C-25 (Pharmacia Fine Chemicals, Sweden) column (1 l), which was previously equilibrated with 0.05 M acetate buffer (pH 4.4).

Elution was carried out with a 0.05 M acetate buffer solution and eluate fractions of 1400 ml to 1600 ml were collected and the eluate was passed through Dowex 50 W×2 column (H+ form; 100 ml).

After the column was washed with 300 ml of water, and elution was carried out with 400 ml of 0.5 N-aqueous ammonia. The eluate was subjected to evaporation to remove the solvent and the residue was lyophilized, whereupon 0.80 g of the title compound was obtained.

$^1$H-NMR δ ppm (in heavy water): 2.35(3H, s, CH$_3$CO—), 2.68(2H, d, —CH$_2$—COO$^\ominus$), 3.22(3H, s, CH$_3$—N—), 3.36(9H, s, (CH$_3$)$_3$N$^\oplus$—), ca3.8(2H, m, (CH$_3$)$_3$N$^\oplus$—CH$_2$—), 5.66(1H, m,

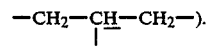

(2) Production of [(R)-2-methylammonio-3-carboxypropyl]trimethylammonium . dichloride:

In 30 ml of 6N-aqueous hydrochloric acid was dissolved 0.50 g of (R)-3-(N-acetyl-N-methylamino)-4-trimethylammoniobutyrate obtained in said item (1), and the solution was treated at 100° C. for 24 hours. The reaction mixture was subjected to evaporation under reduced pressure to remove the solvent, and to the residue was added 30 ml of water, and further the mixture was subjected to evaporation under reduced pressure to remove the solvent. After the residue was well dried under reduced pressure, the residue was dissolved in a small amount of water and lyophilized to give 0.45 g of the title compound as oily product.

1H-NMR δ ppm (in heavy water): 3.12(3H, s, CH$_3$—NH—), 3.39(2H, d, —CH$_2$—COO$^\ominus$), 3.52(9H, s, (CH$_3$)$_3$N$^\oplus$—), 4.18(2H, d, (CH$_3$)$_3$N$^\ominus$—CH$_2$—), 4.45(1H, m, $-CH_2-\underline{CH}-CH_2-$).

EXAMPLE 20

Production of [(R)-2-ethylammonio-3-carboxypropyl]-trimethylammonium . dichloride:

(1) Production of (R)-3-(N-acetyl-N-ethylamino)-4-trimethylammoniobutyrate:

In 40 ml of dimethylformamide was dissolved 1.9 g of FA-5859 (free form) obtained in the manner of Reference Example 2, and to the mixture were added 6 ml of ethyl iodide and 1.4 g of sodium hydride in oil. The reaction mixture was stirred at 75° C. for 10 hours, and the precipitates were removed by filtration. Dimethylformamide was removed by evaporation under reduced pressure, and to the residue were added 20 ml of methanol and 30 ml of 1N aqueous sodium chloride, and then the mixture was stirred 2 hours at room temperature.

After methanol was removed by evaporation, the residue was dissolved in 100 ml of water and the solution was passed through a Dowex 50 W×2 column ($H^+$ form; 100 ml).

After washing the column with 300 ml of water, elution was carried out with 400 ml of 0.5 N-aqueous ammonia. The eluate was subjected to evaporation to remove the solvent, and the oily residue, which was 1.4 g, was dissolved in 20 ml of water. The solution was passed through a CM-Sephadex C-25 column (1 l), which was previously equilibrated with 0.05 M acetate buffer (pH 4.4).

Elution was carried out with 0.05 M acetate buffer and eluate fractions of 1450 ml to 1600 ml were collected and the eluate was passed through Dowex 50 W×2 column ($H^+$ form; 60 ml).

After the column was washed with 200 ml of water, and eluation was carried out with 200 ml of 0.5 N-aqueous ammonia. The eluate was subjected to evaporation to remove the solvent and the residue was liophilized, whereupon 0.41 g of the title compound was obtained.

$^1$H-NMR δ ppm (in heavy water): 1.48(3H, t, $-N-CH_2CH_3$), 2.39(3H, s, $-N-COCH_3$) 2.78(2H, d, $-CH_2-COO^\ominus$), 3.35(9H, s, $(CH_3)_3N^\oplus-$), 3.3–4.2(4H, m, $-N-\underline{CH_2}-CH_3, (CH_3)_3N^\oplus-\underline{CH_2}-$), 5.40

(1H, m, $-\underline{CH}-CH_2-COO^\ominus$)

(2) Production of [(R)-2-ethylammonio-3-carboxypropyl]trimethylammonium . dichloride:

In 30 ml of 6N-aqueous hydrochloric acid was dissolved 0.25 g of (R)-3-(N-acetyl-N-ethylamino)-4-trimethylammoniobutyrate obtained in said item (1), and the solution was treated at 100° C. for 24 hours. The reaction mixture was subjected to evaporation under reduced pressure, and to the residue was added 20 ml of water, and further the mixture was subjected to evaporation under reduced pressure. After the residue was well dried under reduced pressure, the residue was dissolved in a small amount of water and lyophilized to give 0.23 g of the title compound as oily product.

$^1$H-NMR δ ppm (in heavy eater): 1.48(3H, t, $-N-CH_2CH_3$), 3.45(2H, d, $-\underline{CH_2}-COO^\ominus$), 3.54(9H, s, $(CH_3)_3N^\oplus-$), ca. 3.7(2H, m, $-N-\underline{CH_2}CH_3$), 4.20(2H, d, $(CH_3)_3N^\oplus-\underline{CH_2}$), 4.45

(1H, m, $-\underline{CH}-CH_2-COO^\ominus$)

EXAMPLE 21

Tablets are prepared by a conventional method employing the following ingredients:

| | |
|---|---|
| (R)-3-benzyloxycarbonylamino-4-trimethylammoniobutyrate | 300 mg |
| Corn starch | 50 mg |
| Lactose | 28 mg |
| Hydroxypropylcellulose-L | 20 mg |
| Magnesium stearate | 2 mg |
| | 400 mg (per tablet) |

The daily dose of the above tablets for human adults is generally 4 to 8 tablets after each meal (3 times a day).

EXAMPLE 22

Tablets are prepared by a conventional method employing the following ingredients:

| | |
|---|---|
| (R)-3-palmitoylamino-4-trimethyl-ammoniobutyrate | 300 mg |
| Corn starch | 50 mg |
| Lactose | 28 mg |
| Hydroxypropylcellulose-L | 20 mg |
| Magnesium stearate | 2 mg |
| | 400 mg (per tablet) |

The daily dose of the above tablets for human adults is generally 2 to 4 tablets after each meal (3 times a day).

EXAMPLE 23

Tablets are prepared by a conventional method employing the following ingredients:

| | |
|---|---|
| [(R)-2-methylammonio-3-carboxy-propyl]trimethylammonium dichloride | 300 mg |
| Corn starch | 50 mg |
| Lactose | 28 mg |
| Hydroxypropylcellulose-L | 20 mg |
| Magnesium stearate | 2 mg |
| | 400 mg (per tablet) |

The daily dose of the above tablets for human adults is generally 2 to 4 tablets after each meal (3 times a day).

EXAMPLE 24

Tablets are prepared by a conventional method employing the following ingredients:

| | |
|---|---|
| [(S)-2-ammonio-3-carboxypropyl]-trimethylammonium dichloride | 300 mg |
| Corn starch | 50 mg |
| Lactose | 28 mg |
| Hydroxypropylcellulose-L | 20 mg |
| Magnesium stearate | 2 mg |
| | 400 mg (per tablet) |

The daily dose of the above tablets for human adults is generally 4 to 8 tablets after each meal (3 times a day).

What we claim is:

1. Aminocarnitines having the structural formula:

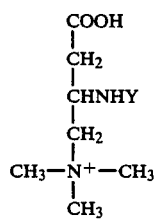

wherein Y is selected from the group consisting of

$$-\overset{O}{\underset{\|}{C}}R$$

wherein R is selected from the group consisting of aliphatic containing from 9+ to 19 carbon atoms, and wherein $X^-$ is a nontoxic counterion; the non-toxic esters and salts thereof; or the zwitterionic form thereof wherein H is removed from the —COOH group and —COO$^-$ serves as the counterion $X^-$ or $Z^-$.

2. A compound of the formula:

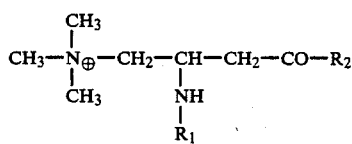

wherein $R_1$ is hydrogen or acyl of one to 18 carbon atoms, the acyl being unsubstituted or substituted by lower alkoxy, halogen, hydroxy, nitro, amino, cyano, sulfo, aryl or aralkyloxy; $R_2$ is hydroxy, alkoxy of one to 6 carbon atoms or amino; provided that when $R_1$ is hydrogen or acetyl, $R_2$ is not hydroxy; or a pharmaceutically acceptable salt thereof.

3. A compound as claimed in claim 2, wherein $R_1$ is hydrogen.

4. A compound as claimed in claim 2, wherein $R_1$ is acyl of one to 18 carbon atoms.

5. A compound as claimed in claim 2, wherein $R_2$ is hydroxy.

6. A compound as claimed in claim 2, wherein $R_2$ is alkoxy of one to 6 carbon atoms.

7. A compound as claimed in claim 2, wherein $R_2$ is amino.

8. A compound as claimed in claim 2, wherein $R_1$ is carbamyl and $R_2$ is hydroxy.

9. A compound as claimed in claim 2, wherein $R_1$ is benzyloxycarbonyl and $R_2$ is hydroxy.

10. A compound as claimed in claim 2, wherein $R_1$ is benzoyl and $R_2$ is hydroxy.

11. A compound as claimed in claim 2, wherein $R_1$ is hydrogen and $R_2$ is methoxy.

12. A compound as claimed in claim 2, wherein $R_1$ is hydrogen and $R_2$ is ethoxy.

13. A compound as claimed in claim 2, wherein $R_1$ is hydrogen and $R_2$ is propoxy.

14. A compound as claimed in claim 2, wherein $R_1$ is a capryl and $R_2$ is methoxy.

15. A compound as claimed in claim 2, wherein $R_1$ is hydrogen and $R_2$ is amimo.

16. A compound as claimed in claim 2, wherein $R_1$ is formyl and $R_2$ is hydroxy.

17. A compound as claimed in claim 2, wherein $R_1$ is myristoyl and $R_2$ is hydroxy.

18. A compound as claimed in claim 2, wherein $R_1$ is palmitoyl and $R_2$ is hydroxy.

19. A compound of the formula:

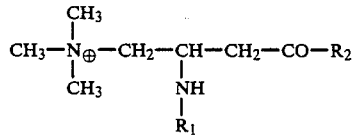

wherein $R_1$ is hydrogen or acyl of 1 to 18 carbon atoms, the acyl being unsubstituted or substituted by lower alkoxy, halogen, hydroxy, unsubstituted by lower alkoxy, halogen, hydroxy, nitro, $NH_2$, cyano, sulfo, phenyl, naphthyl or phenyl-$C_{1-4}$ alkoxy; $R_2$ is hydroxy, alkoxy of 1 to 6 carbon atoms or $NH_2$: or a pharmaceutically acceptable salt thereof.

20. A compound of claim 19, wherein $R_1$ is hydrogen.

21. A compound of claim 19, wherein $R_1$ is acyl of 1 to 18 carbon atoms.

* * * * *

UNITED STATES PATENT AND TRADEMARK OFFICE
CERTIFICATE OF CORRECTION

PATENT NO. : 4,948,534
DATED : August 14, 1990
INVENTOR(S) : Susumu SHINAGAWA et al.

It is certified that error appears in the above-identified patent and that said Letters Patent is hereby corrected as shown below:

In column 29:
In claim 1 next to the formula:

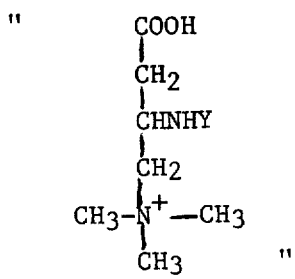

insert --X⁻--.

In column 29, line 23, delete "9+" and insert --9--.

Signed and Sealed this

Seventh Day of April, 1992

Attest:

HARRY F. MANBECK, JR.

*Attesting Officer*     *Commissioner of Patents and Trademarks*